United States Patent
Ide

(10) Patent No.: US 7,524,290 B2
(45) Date of Patent: Apr. 28, 2009

(54) SYSTEM AND METHOD OF NON-INVASIVE BLOOD PRESSURE MEASUREMENTS AND VASCULAR PARAMETER DETECTION IN SMALL SUBJECTS

(75) Inventor: Andrew H. Ide, Torrington, CT (US)

(73) Assignee: The Kent Scientific Corporation, Torrington, CT (US)

( * ) Notice: Subject to any disclaimer, the term of this patent is extended or adjusted under 35 U.S.C. 154(b) by 0 days.

(21) Appl. No.: 11/410,174

(22) Filed: Apr. 24, 2006

(65) Prior Publication Data

US 2006/0247540 A1 Nov. 2, 2006

Related U.S. Application Data

(60) Provisional application No. 60/676,647, filed on Apr. 29, 2005.

(51) Int. Cl.
*A61B 5/02* (2006.01)
(52) U.S. Cl. .................... 600/490; 600/481; 600/485
(58) Field of Classification Search ............... 600/499; 606/202
See application file for complete search history.

(56) References Cited

U.S. PATENT DOCUMENTS

| | | | |
|---|---|---|---|
| 1,667,409 A | | 9/1928 | Barr |
| 2,540,163 A | | 2/1951 | Brosene, Jr. et al. |
| 3,104,661 A | | 9/1963 | Halpern |
| 3,149,492 A | | 9/1964 | Weinberg |
| 3,348,534 A | * | 10/1967 | Marx et al. ............... 600/492 |
| 3,572,320 A | | 3/1971 | Gerold et al. |
| 3,847,142 A | * | 11/1974 | Williams et al. ............ 600/507 |
| 6,202,570 B1 | | 3/2001 | Kurtsman |
| 6,203,210 B1 | | 3/2001 | Mikula et al. |
| 2005/0070805 A1 | * | 3/2005 | Dafni ........................ 600/492 |

OTHER PUBLICATIONS

Ischemia. The American Heritage® Dictionary of the English Langauge. Copyright © 2007, 2000 by Houghton Mifflin Company. Retrieved Mar. 26, 2008 from http://www.credoreference.com/entry/7073917.*
Hellstrom B., Heat vasodilatation of rat tail., Can J. Physiol Pharmacol, Apr. 1975; 53(2): 202-6.
Berry JJ, et al., Thermoregulatory responses of rats to varying environmental temperatures., Aviat Space Environ Med., Jun. 1984; 55(6): 546-9.

(Continued)

*Primary Examiner*—Patricia C Mallari
(74) *Attorney, Agent, or Firm*—McCormick, Paulding & Huber LLP

(57) ABSTRACT

A system and method for taking non-invasive blood pressure and other vascular parameter measurements includes placing a vascular compression device about an appendage of a subject. An arterial/venous occlusion cuff is placed about a base of the appendage. The vascular compression device is activated to generate compression ischemia in the appendage. The arterial/venous occlusion cuff is pressurized to generate arterial/venous occlusion in the appendage. The vascular compression device is deactivated. The arterial/venous occlusion cuff is gradually depressurized to allow blood and other body fluids to flow into the appendage and thereupon determine vascular parameters such as, for example, systolic arterial blood pressure, diastolic arterial blood pressure, venous blood pressure, arterial blood flow, blood vessel compliance, and appendage blood volume.

6 Claims, 4 Drawing Sheets

OTHER PUBLICATIONS

Owens NC, et al., Thermoregulatory control of sympathetic fibres supplying the rat's tail., J Physiol., Sep. 15, 2002; 543(Pt 3): 849-58.

Sakurada S., et al., Relationship between body core and peripheral temperatures . . . , Jpn J Physiol., 1993; 43(5): 659-67.

Raman ER, et al., Body temperature control of rat tail blood flow., Am J Physiol., Sep. 1983; 245(3): R426-32.

Raman ER, et al., Mathematical circulation model for the blood-flow-heat-loss relationship in the rat tail., Phys Med Biol., Jul. 1987; 32(7): 859-75.

Sakurada S., et al., Mechanism of vasoconstriction in the rat's tail when warmed locally., J Appl Physiol., Nov. 1991; 71(5): 1758-63.

Young AA, et al., Evidence for on-off control of heat dissipation from the tail of the rat., Can J Physiol Pharmacol., Mar. 1982; 60(3): 392-8.

O'Leary DS, et al., Mode of neural control mediating rat tail vasodilation during heating., J Appl Physiol., Nov. 1985; 59(5): 1533-8.

Nakajima Y., et al., Comparison between tail skin blood flow measurements by ultrasonic . . . , Jpn J Physiol., Feb. 1999; 49(1): 121-4.

O'Leary DS, et al., Baroreflex control of the rat tail circulation in normothermia and hyperthermia., J Appl Physiol., Mar. 1989; 66(3): 1234-41.

Vanhoutte G., et al., In-vivo non-invasive study of the thermoregulatory function . . . , NMR Biomed., Jun. 2002; 15(4): 263-9.

Wu Y., et al., A non-uniform three-dimensional perfusion model of rat tail heat transfer., Phys Med Biol., May 1995; 40(5): 789-806.

Reinecke RM., Arterial barostasis along the mouse tail between different steady-state flows., Am J Physiol., Feb. 1977; 232(2): H197-203.

Borg E, et al., Role of heating in non-invasive blood pressure measurements in rats., Acta Physiol Scand., Jan. 1980; 108(1): 73-5.

Kuwahara M, et al., Evaluation of new tail-cuff method for blood pressure measurements . . . , Jikken Dobutsu., Jul. 1991; 40(3): 331-6.

Sakamaki T., et al., Measurement of mean arterial pressure in rats by a tail-cuff method . . . , Jikken Dobutsu., Oct. 1987; 36(4): 409-14.

Bunag RD, Facts and fallacies about measuring blood pressure in rats., Clin Exp Hypertens A., 1983; 5(10): 1659-81.

Bunag RD, et al., Regional vascular influences on tail-cuff measurements of drug-induced . . . , J Appl Physiol., Nov. 1975; 39(5): 724-7.

Ferrari AU, et al., Intra-arterial pressure alterations during tail-cuff blood pressure measurements . . . , J Hypertens., Oct. 1990; 8(10): 909-11.

Widdop RE, et al., A simple versatile method for measuing tail cuff systolic blood pressure in . . . , Clin Sci (Lond)., Sep. 1997; 93(3): 191-4.

Wen SF, et al., An impedance method for blood pressure measurement in awake rats . . . , Hypertension., Apr. 1988; 11(4): 371-5.

Whitesall SE, et al., Comparison of simultaneous measurement of mouse systolic arterial . . . , Am J Physiol Heart Circ Physiol., Feb. 12, 2004 [Epub ahead of print].

Yasufumi Nakajima, et al., Comparison Between Tail Skin Blood Flow Measurements by Ultrasonic Doppler Flowmetry and Plethysmography during Heating in Anesthetized Rats, Japanese Journal of Physiology vol. 49, No. 1, pp. 121-124, 1999.

Clark, E.W., et al., The measurement of the flow of blood through the hind paw of a mouse by venous occlusion plethysmography, Department of physiology, The Queen's University of Belfast, Physiological Society, Sep. 1969.

* cited by examiner

SYSTEM AND METHOD OF NON-INVASIVE BLOOD PRESSURE MEASUREMENTS AND VASCULAR PARAMETER DETECTION IN SMALL SUBJECTS

CROSS-REFERENCE TO RELATED APPLICATION

This application claims the benefit of U.S. Provisional Application No. 60/676,647, filed on Apr. 29, 2005, the disclosure of which is hereby incorporated by reference in its entirety.

FIELD OF THE INVENTION

This invention relates generally to a system and method of taking blood pressure and other vascular parameter measurements, and more particularly to taking non-invasive blood pressure and other vascular parameter measurements in small subjects.

BACKGROUND OF THE INVENTION

Monitoring blood pressure and vascular parameters in small subjects such as companion animals, research animals, infants and preemies is an important diagnostic and research tool. Taking direct arterial blood pressure measurements can be painful, injurious, lead to further complications, and the direct method can only be acute in nature.

Non-invasive blood pressure measurement has become an essential part of modern medicine and research. Current methods generally involve a vascular occlusion cuff around an appendage and some method of detecting arterial pulsations. Methods for detecting arterial pulsations include photoelectric sensors, piezoelectric sensors, microphones, stethoscope, ultrasonic flow probes, secondary pneumatic cuffs or the occlusion cuff itself.

The procedure generally includes applying pressure to the appendage to compress the underlying arteries by inflating and pressurizing the arterial/venous vascular occlusion cuff until arterial blood flow ceases as determined by pulse termination from the pulse detector. Blood pressure readings are taken either while compression is being applied or while compression is being released. The pressure in the arterial/venous vascular occlusion cuff at the time of pulse termination or pulse initiation is universally accepted as the systolic blood pressure. Diastolic blood pressure is often taken as a return to nearly full amplitude of the pulse signal.

In smaller subjects, arterial pulsations are significantly smaller and of higher frequency. Subjects having 20 grams or smaller body weight such as mice have become the mainstay of modern medical research. These subjects have extremely small, high frequency pulsations that are almost impossible to detect with the above mentioned methods.

Venous occlusion plethysmography has been used as a method to access the health of peripheral vasculature in humans for decades. Generally, the technique involves placing an arterial/venous vascular occlusion cuff on the appendage proximal to a device that will measure the swelling of the appendage also known as a plethysmograph. The plethysmograph is a second, long pneumatic cuff, series of strain gages wrapped around the distal portion of the appendage, impedance or capacitance electrodes. The arterial/venous occlusion cuff is inflated to exert sufficient pressure to occlude the veins and stop the flow of venous blood out of the appendage. Blood flow into the appendage from the arteries keeps filling the vasculature which swells the appendage. The plethysmograph measures the swelling volume from which vascular parameters are determined.

Non-invasive blood pressure and vascular readings are also taken using arterial/venous occlusion plethysmography. This type of reading depends on the capacity of the appendage to swell or engorge during venous occlusion. Detection of the parameters in subjects with hypertensive or hyperemic appendages is difficult since the appendage is already supersanguinated and the surrounding vasculature is distended leaving little compliance for additional swelling.

Accordingly, it is an object of the present invention to provide a system and method for taking non-invasive blood pressure and other vascular parameter measurements in small subjects that overcomes the above-mentioned drawbacks and disadvantages.

SUMMARY OF THE INVENTION

In one aspect of the present invention, a method for taking non-invasive blood pressure and other vascular parameter measurements includes placing a vascular compression device about an appendage of a subject. An arterial/venous occlusion cuff is placed about a base of the appendage. The vascular compression device is activated to generate compression ischemia in the appendage. The arterial/venous occlusion cuff is pressurized to generate arterial/venous occlusion in the appendage. The vascular compression device is then deactivated. The arterial/venous occlusion cuff is depressurized gradually to allow blood and other body fluids to flow slowly into the appendage and thereupon determine vascular parameters such as, for example, systolic arterial blood pressure, diastolic arterial blood pressure, venous blood pressure, arterial blood flow, blood vessel compliance, and appendage blood volume as measured, for example, from a volume plethysmograph on the appendage.

In another aspect of the present invention, a system for taking non-invasive blood pressure and other vascular parameter measurements includes a vascular compression device to be coupled to an appendage of a subject. An arterial/venous occlusion cuff is to be coupled to a base of the appendage, and a volume measuring device such as a volume plethysmograph to measure volume changes of the appendage. A plethysmograph controller communicates with at least one of the vascular compression device, the volume plethysmograph and the arterial/venous occlusion cuff for determining vascular parameters.

DETAILED DESCRIPTION OF THE PREFERRED EMBODIMENTS

Figure 1:
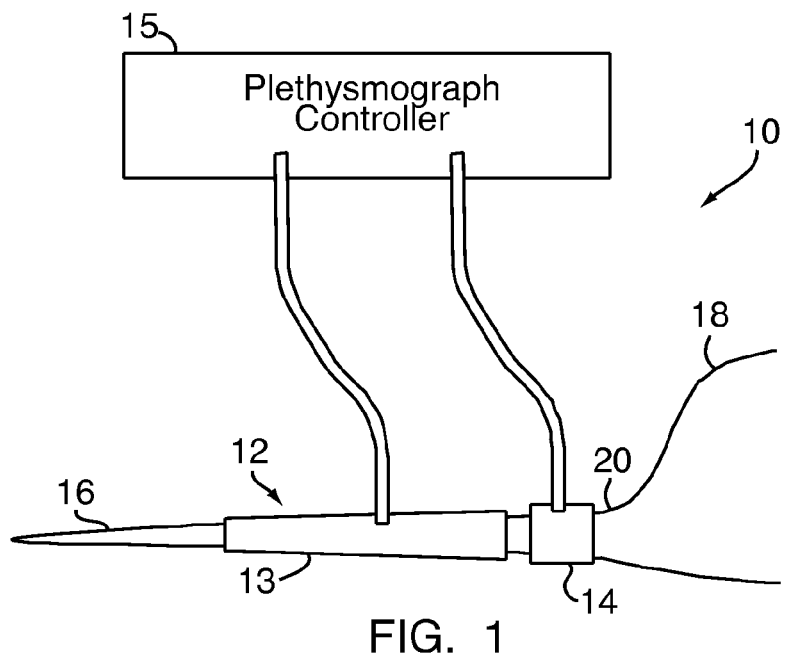
FIGS. 1, 1a & 1b schematically illustrate a compression device being used for measuring blood pressure and other vascular parameters in accordance with the present invention.
Figure 1A:
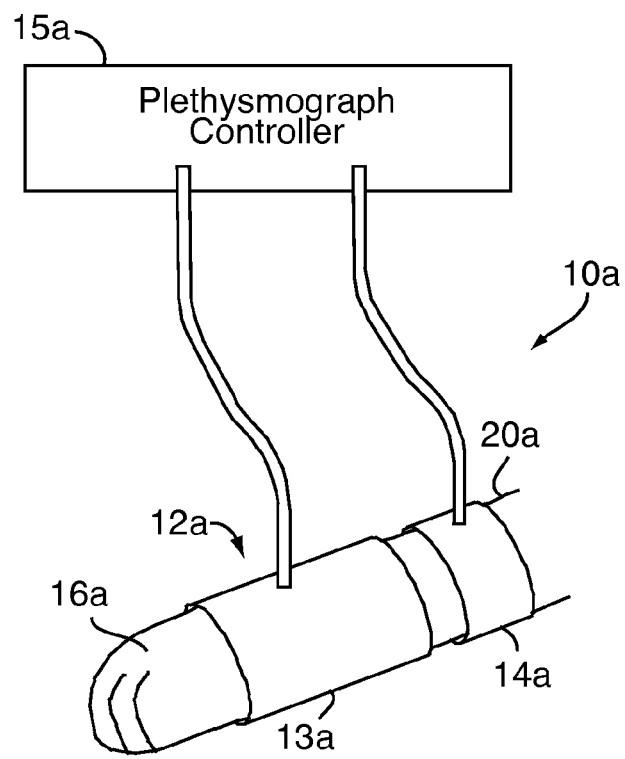
Figure 1B:
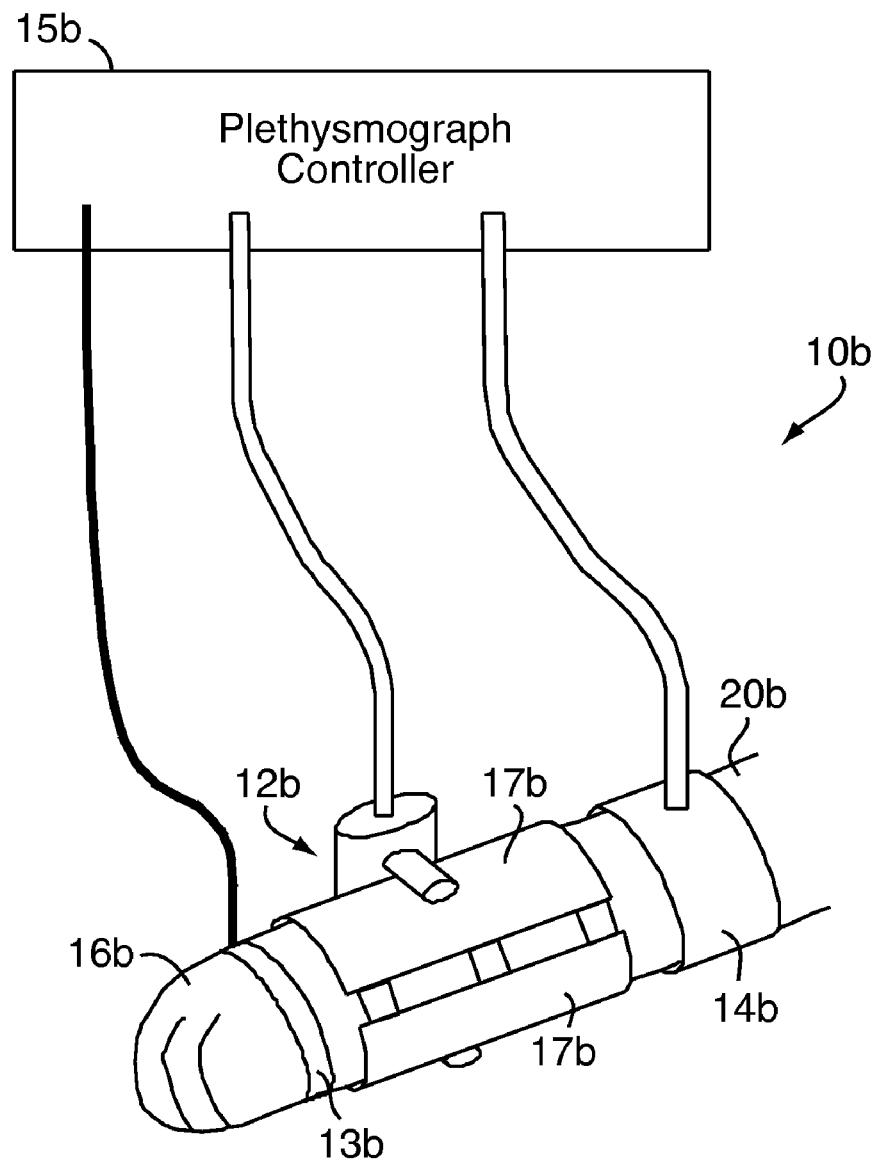

Referring to FIGS. 1, 1a & 1b, a compression system for taking blood pressure and other vascular parameter measurements in the appendages of small subjects is indicated generally by the reference numbers 10, 10a & 10b. The compression system 10, 10a & 10b comprises a vascular compression device 12, 12a & 12b, a volume measuring device such as a volume plethysmograph 13, 13a & 13b and an arterial/venous vascular occlusion cuff 14, 14a & 14b. A plethysmograph controller 15, 15a & 15b communicates with one or more of the vascular compression devices 12, 12a & 12b, volume plethysmograph 13, 13a & 13b and the occlusion cuffs 14, 14a & 14b. Although the plethysmograph controller 15, 15a & 15b, is schematically illustrated as a separate component, the plethysmograph controller can be incorporated into the vascular compression device 12, 12a & 12b, volume plethysmograph 13, 13a & 13b and the arterial/venous occlusion cuff 14, 14a & 14b. The plethysmograph controller 15, 15a, 15b includes conventional electronics such as transducer, amplifiers, etc. to derive the signals from the sensors on the appendage, and also includes conventional electromechanical devices such as pumps, valves, actuators, etc. to control the arterial/venous occlusion cuff 14, 14a & 14b, vascular compression devices 12, 12a & 12b and volume plethysmograph 13, 13a & 13b. As shown in FIGS. 1, 1a & 1b, the vascular compression device 12, 12a & 12b is coupled to an appendage 16, 16a & 16b of a small subject 18 such as, for example, the tails, arms or legs of rodents, cats, dogs, premature infants, etc. Moreover, the vascular occlusion cuff 14, 14a & 14b is coupled to the base 20, 20a & 20b of the appendage for the purpose explained below.

The compression system 10, 10a & 10b and its method of use improves non-invasive blood pressure measurements and vascular parameter detection in the appendages of small subjects by compression ischemia prior to vascular occlusion. In accordance with the present invention, an appendage is first compressed by mechanical means such as by activation of the vascular compression device 12, 12a & 12b to empty the vasculature and cause ischemia prior to arterial/venous occlusion by pressurization of the arterial/venous occlusion cuff 14. After occlusion, the compression is removed by deactivation of the vascular compression device 12, 12a & 12b. A traditional technique of arterial/venous occlusion plethysmography is then applied to measure the swelling of the appendage as the arterial occlusion is gradually removed by depressurization of the arterial/venous vascular occlusion cuff 14, 14a & 14b so as to derive blood pressure and vascular parameters.

The compression ischemia method in accordance with the present invention provides much larger readings from small subjects with hyperemic or hypertensive appendages relative to conventional measuring techniques. Along with systolic and diastolic arterial blood pressure, other vascular parameters are also detected which are not possible with the other described conventional techniques. These vascular parameters include venous blood pressure, arterial blood flow, blood vessel compliance and appendage blood volume which are useful in determining the vascular health of a subject.

In FIGS. 1 and 1a, the volume plethysmograph (i.e. volume/pressure recording (VPR) sensing cuff) 13 & 13a and the vascular compression device 12 & 12a are the same device configured for use in two different modes. First, as the vascular compression device 12 & 12a, the VPR cuff is pressurized to a high pressure to cause evacuation of blood from the appendage. Secondly, the VPR cuff is then pressurized to a low pressure to function as the volume plethysmograph 13 & 13a.

In FIG. 1b, the vascular compression device 12b is structurally separate and distinct from the volume plethysmograph sensing device 13b. As illustrated, the vascular compression device 12b is a mechanical device such as two plates 17b that are operated by an electric motor, pneumatic cylinder, or other actuator. The vascular compression device 12b is placed on the appendage such that when the actuator is activated, pressure is applied to the appendage to cause the evacuation of blood from the appendage. Volume change in the appendage from the inflow of blood and other body fluids is measured by strain gages, impedance or capacitance electrodes, or other electronic means 13b.

Specifically, the blood pressure readings are determined by appendage swelling or engorgement of blood and body fluids following occlusion. For example, blood pressure measurements can be determined on small animal appendages by monitoring or sensing the inflow of blood and other body fluids into the portion of the appendage distal to an occlusion cuff. The sensing method monitors the overall fluid volume from the initial release of the occlusion pressure until after cessation of venous occlusion.

Engorgement or swelling can be sensed by an electronic transducer using pneumatics or hydraulics, skin impedance, strain gauges or capacitance. Hydraulics and pneumatics can also be used with water or mercury filled manometers, fluid filled columns or pressure gages. Generally, when using hydraulics or pneumatics, a volume/pressure recording (VPR) pneumatic or hydraulic sensing cuff (i.e. volume plethysmograph) is placed on the appendage. Appendage swelling or engorgement is determined by an increase in pressure in the volume/pressure recording (VPR) sensing cuff measured by an electronic pressure transducer in the plethysmograph controller. Skin impedance measures the resistance of the appendage as it changes size or shape as the appendage swells or engorges with blood. Strain gauges applied to the appendage measure the change in size or shape by changing the resistance of a Wheatstone bridge as the appendage is deformed by the inflow of blood. Capacitance measures the change in capacitance because of changes in the size or shape of the appendage.

As an example, VPR technology can employ a volume/pressure recording (VPR) pneumatic sensing cuff that is pressurized to extend the cuff bladder to a pressure that is lower than venous pressure, typically 30 mm Hg. The low pressure in the VPR cuff ensures that the cuff bladder is in intimate contact with the surface of the appendage. An extremely sensitive, differential air pressure transducer is used to measure the pressure changes above or on top of the applied pressure. To measure the small pressures developed by the engorgement or swelling of the appendage, the pressure from the VPR cuff is directed to both the positive and negative ports of the electronic differential pressure transducer. By applying the same high pressure to both ports of the differential transducer, the net result is zero pressure.

When the measurement is to be taken, the transducer ports are isolated, with the negative port having a static pressure of 30 mm Hg and the positive port connected to the VPR cuff which is on the animal appendage. As the appendage swells or engorges, the volume of the VPR cuff is displaced, causing a pressure increase which is detected by the electronic differential transducer in the plethysmograph controller.

A delay period is used after vascular occlusion to cause an additional ischemic response which may help in blood pressure determination. Readings for systolic blood pressure are determined at the start of swelling as determined by the point of the pressure increase in the appendage. As the appendage continues to swell or engorge, it continues to do so more and more rapidly until it reaches a maximum rate of change or slope. Diastolic blood pressure is determined at the point of the maximum slope of the swelling signal.

Venous blood pressure is determined at the point when the blood is permitted to flow out of the appendage through the veins. This point is when the VPR signal reaches a maximum and starts decreasing or plateaus.

Low or high pressure compression of an appendage with the vascular compression device 12, 12a & 12b causes a displacement of body fluid volume in the soft tissues of the appendage. While the appendage is being compressed by the vascular compression device 12, 12a & 12b, arterial/venous vascular occlusion is applied at a point proximal to the initial compression by the vascular occlusion cuff 14, 14a & 14b, the displaced fluids as well as additional fluids are prevented from entering the distal portion of the appendage. The compression of the appendage by the vascular compression device 12, 12a & 12b is removed after arterial/venous vascular occlusion providing a space or cavity for the body fluids to flow during the release of the occlusion pressure. As given by way of example above with respect to FIGS. 1, 1a and 1b it has been discovered that the compression of the tail or appendage of an animal or other patient induces an ischemic condition in the appendage which can assist in the appendage requesting additional body fluid volume.

Figure 2:
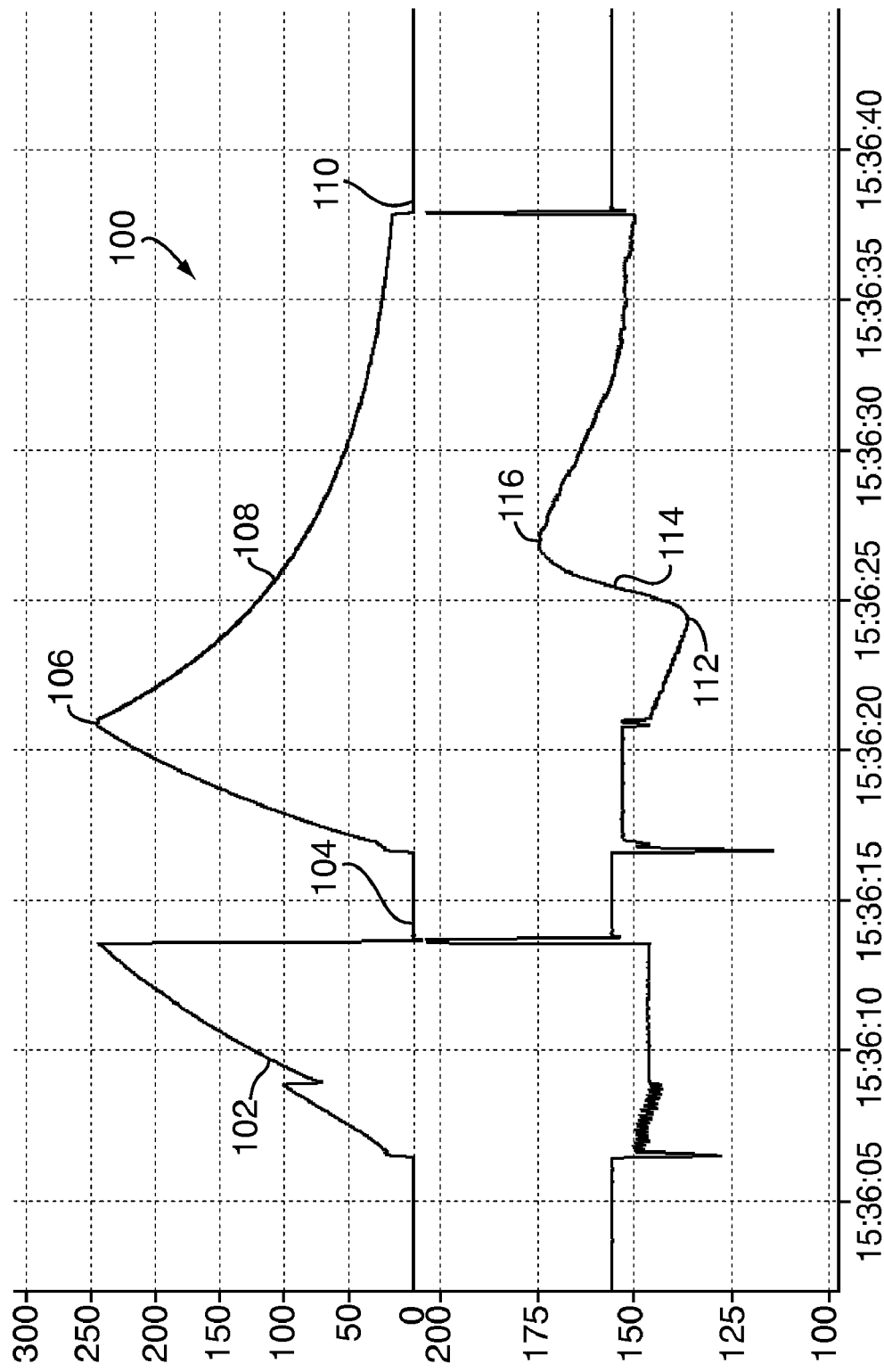
FIG. 2 is a graph recording of a patient's appendage showing vascular responses following compression ischemia as measured with a volume/pressure recording pneumatic sensing cuff (volume plethysmograph) in accordance with the present invention.

With reference to FIG. 2, a graph of recording from a patient's appendage showing vascular responses following compression ischemia as measured with volume/pressure recording (VPR) sensing cuff in accordance with the present invention is indicated generally by the reference number 100. Pneumatic compression of the appendage with the vascular compression device is indicated at 102. Arterial/venous occlusion with the vascular occlusion cuff is indicated at 104. Maximum occlusion cuff pressure is indicated at 106. Slow release of the pressure in the occlusion cuff to determine vascular parameters is indicated at 108. Release of pressure and venting of the occlusion cuff is indicated at 110. Volume recording of the VPR cuff from which vascular parameters are taken is indicated at 112, 114 and 116. Specifically, volume of appendage starting to increase as occlusion cuff pressure drops below systolic arterial blood pressure is indicated at 112. Rate of change of swelling reaching maximum at diastolic arterial blood pressure is indicated at 114. Swelling ceasing as occlusions cuff pressure drops below venous blood pressure and blood can flow back to the body is indicated at 116.

Figure 3:
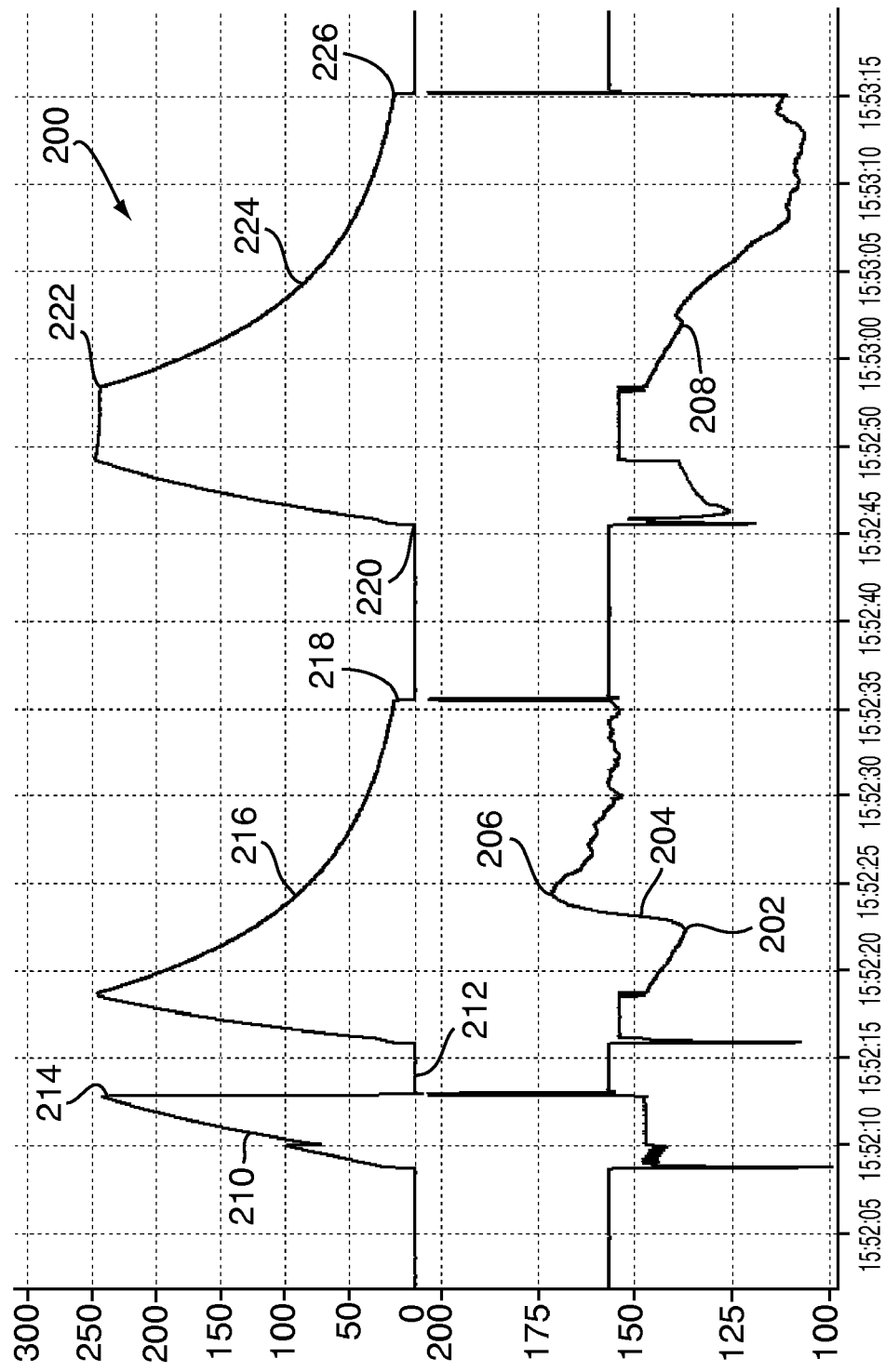
FIG. 3 is a graph showing a comparison of compression ischemia occlusion volume plethysmography in accordance with the present invention with a conventional method taken on the same patient as measured with volume/pressure recording pneumatic sensing cuff (volume plethysmograph).

FIG. 3 is a graph 200 showing a comparison of a compression ischemic venous occlusion plethysmography, indicated at 202, 204 and 206, in accordance with the present invention with a conventional method indicated at 208 on the same patient as measured with volume/pressure recording (VPR) sensing cuff. A vascular occlusion recording in accordance with the present invention is initiated with pneumatic compression indicated at 210, 212, 214, 216 and 218. The arterial/venous vascular occlusion recording is then completed with a conventional method without compression indicated at 220, 222, 224 and 226. Note the large response in the VPR cuff signal at 202, 204 and 206 with compression ischemia compared to the relatively nonexistent response indicated at 208 without compression.

As will be recognized by those of ordinary skill in the pertinent art, numerous modifications and substitutions can be made to the above-described embodiments of the present invention without departing from the scope of the invention. Accordingly, the preceding portion of this specification is to be taken in an illustrative, as opposed to a limiting sense.

What is claimed is:

1. A method for taking non-invasive blood pressure and other vascular parameter measurements, the method comprising the steps of:
    placing an arterial/venous occlusion cuff about a base of an appendage of a small subject;
    placing the vascular compression device about the appendage distal to the occlusion cuff;
    activating the vascular compression device to generate compression ischemia in the appendage;
    pressurizing the arterial/venous occlusion cuff to generate arterial/venous occlusion in the appendage;
    deactivating the vascular compression device;
    depressurizing the arterial/venous occlusion cuff to allow blood to flow into the appendage and thereupon determine vascular parameters; and
    measuring a volume change of the appendage distal to the occlusion cuff with a volume measuring device during the step of depressurizing the arterial/venous occlusion cuff to determine the vascular parameters.

2. A method as defined in claim 1, wherein the steps of activating and deactivating the vascular compression device is accomplished by one of pneumatically, hydraulically and mechanically.

3. A method as defined in claim 1, wherein the steps of pressurizing and depressurizing the arterial/venous occlusion cuff is accomplished pneumatically.

4. A method as defined in claim 1, wherein the step of depressurizing the arterial/venous occlusion cuff is accomplished gradually.

5. A method as defined in claim 1, wherein the step of measuring a volume change includes providing a plethysmograph controller communicating with at least one of the vascular compression device, the volume measuring device and the arterial/venous occlusion cuff.

6. A method as defined in claim 1, wherein the vascular parameters include at least one of systolic arterial blood pressure, diastolic arterial blood pressure, venous blood pressure, arterial blood flow, blood vessel compliance, and appendage blood volume.

* * * * *